United States Patent
Abreu Oramas

(10) Patent No.: US 10,492,725 B2
(45) Date of Patent: Dec. 3, 2019

(54) METHOD AND SYSTEM OF FACILITATING MONITORING OF AN INDIVIDUAL BASED ON AT LEAST ONE WEARABLE DEVICE

(71) Applicant: Orlando Efrain Abreu Oramas, West Palm Beach, FL (US)

(72) Inventor: Orlando Efrain Abreu Oramas, West Palm Beach, FL (US)

(*) Notice: Subject to any disclaimer, the term of this patent is extended or adjusted under 35 U.S.C. 154(b) by 0 days.

(21) Appl. No.: 16/173,162

(22) Filed: Oct. 29, 2018

(65) Prior Publication Data

US 2019/0125264 A1  May 2, 2019

Related U.S. Application Data

(60) Provisional application No. 62/578,437, filed on Oct. 29, 2017.

(51) Int. Cl.
 *A61B 5/00* (2006.01)

(52) U.S. Cl.
 CPC .......... *A61B 5/6824* (2013.01); *A61B 5/4839* (2013.01); *A61B 5/7225* (2013.01); *A61B 5/746* (2013.01); *A61B 2562/0219* (2013.01)

(58) Field of Classification Search
 None
 See application file for complete search history.

(56) References Cited

U.S. PATENT DOCUMENTS

| | | | | |
|---|---|---|---|---|
| 8,894,577 B2* | 11/2014 | Reed | ..................... | A61B 5/0002 600/301 |
| 8,968,196 B2* | 3/2015 | Teller | ....................... | A61B 5/01 600/301 |
| 2011/0245633 A1* | 10/2011 | Goldberg | ............... | A61B 5/681 600/301 |
| 2012/0149996 A1* | 6/2012 | Stivoric | ................... | A61B 5/01 600/301 |
| 2014/0115008 A1* | 4/2014 | Stivoric | ............. | G06Q 30/0242 707/796 |
| 2014/0135592 A1* | 5/2014 | Ohnemus | ............. | A61B 5/7275 600/301 |
| 2014/0172310 A1* | 6/2014 | Chin | ........................ | G06F 19/00 702/19 |
| 2014/0206289 A1* | 7/2014 | Rahman | ................... | H04W 4/80 455/41.2 |
| 2015/0094544 A1* | 4/2015 | Spolin | ................... | A61B 5/7275 600/301 |

(Continued)

*Primary Examiner* — Fekadeselassie Girma

(57) ABSTRACT

A method of facilitating the monitoring of an individual based on at least one wearable device is disclosed. The method may include receiving, using a communication device, at least one physiological data from a user device associated with the individual. Further, the method may include retrieving, using a storage device, at least one analyzing criterion based on the user identifier. Further, the method may include analyzing, using a processing device, the at least one physiological data based on the at least one analyzing criterion. Further, the method may include generating, using the processing device, at least one notification based on the analyzing. Further, the method may include retrieving, using the storage device, at least one watcher identifier based on the user identifier. Further, the method may include transmitting, using the communication device, the at least one notification to at least one watcher device associated with the at least one watcher identifier.

12 Claims, 14 Drawing Sheets

(56) References Cited

U.S. PATENT DOCUMENTS

| | | | |
|---|---|---|---|
| 2015/0199484 A1* | 7/2015 | Morris | G16H 50/20 |
| | | | 705/2 |
| 2015/0305675 A1* | 10/2015 | Miller | A61B 5/0205 |
| | | | 600/301 |
| 2015/0324568 A1* | 11/2015 | Publicover | G06F 21/64 |
| | | | 726/19 |
| 2016/0235374 A1* | 8/2016 | Miller | A61B 5/7275 |
| 2018/0060518 A1* | 3/2018 | Pappas | G06F 19/00 |
| 2018/0218268 A1* | 8/2018 | Kozloski | G06N 3/008 |

* cited by examiner

METHOD AND SYSTEM OF FACILITATING MONITORING OF AN INDIVIDUAL BASED ON AT LEAST ONE WEARABLE DEVICE

The current application claims a priority to the U.S. Provisional Patent application Ser. No. 62/578,437 filed on Oct. 29, 2017.

FIELD OF THE INVENTION

The present invention relates generally to data processing. More specifically, the present invention describes methods and systems for facilitating the monitoring of an individual.

BACKGROUND OF THE INVENTION

Conventionally, it takes a lot of time and effort to monitor vital signs of users. Often, the users have to visit doctors or specialized laboratories to obtain measurements of their vital signs. Further, many users suffer from mental health issues such as depression. It is difficult for such users to monitor their own stress level. According to the Centers for Disease Control (CDC), depression affects 20-25% of Americans with ages of 18 and over every year. Further, according to National Alliance on Mental Illness (NAMI), only half of all Americans experiencing an episode of major depression received treatment. This may result in an increase in the number of suicides.

Nowadays some smart devices are available for monitoring vital signs of users. However, these devices are not well designed to monitor vital signs. Specifically, these devices do not provide a complete solution for monitoring vital signs, providing support services, alerting loved ones, and providing medication during emergencies. Further, these devices do not track emotions, and do not provide sentimental support in cases such as depression.

Therefore, there is a need for improved systems for facilitating monitoring of individuals, that may overcome one or more of the above-mentioned problems and/or limitations.

SUMMARY

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a method of facilitating the monitoring of a user based on at least one wearable device is disclosed. The method may include receiving, using a communication device, at least one physiological data from a user device associated with the user. Further, the user device may be configured for receiving the at least one physiological data from at least one wearable device worn by the user. Further, the at least one wearable device may include at least one physiological sensor configured for generating the at least one physiological data. Additionally, the at least one physiological data may be associated with a user identifier of the user. The method may include retrieving, using a storage device, at least one analyzing criterion based on the user identifier. Further, the method may include analyzing, using a processing device, the at least one physiological data based on the at least one analyzing criterion. Further, the method may include generating, using the processing device, at least one notification based on the analyzing. Further, the method may include retrieving, using the storage device, at least one watcher identifier based on the user identifier. Further, the at least one watcher identifier may be associated with at least one watcher registered to receive the at least one notification in association with the individual. Further, the method may include transmitting, using the communication device, the at least one notification to at least one watcher device associated with the at least one watcher identifier.

In some embodiments, the present invention comprises a system for facilitating the monitoring of a user based on at least one wearable device is disclosed. The system may include a communication device configured for receiving at least one physiological data from a user device associated with the individual. Further, the user device may be configured for receiving the at least one physiological data from at least one wearable device worn by the individual. Further, the at least one wearable device may include at least one physiological sensor configured for generating the at least one physiological data. Further, the at least one physiological data may be associated with a user identifier of the individual. Further, the communication device may be configured for transmitting at least one notification to at least one watcher device associated with at least one watcher identifier. Further, the system may include a processing device configured for analyzing the at least one physiological data based on at least one analyzing criterion. Further, the processing device may be configured for generating at least one notification based on the analyzing. Further, the system may include a storage device configured for retrieving the at least one analyzing criterion based on the user identifier. Further, the storage device may be configured for retrieving the at least one watcher identifier based on the user identifier. Further, the at least one watcher identifier may be associated with at least one watcher registered to receive the at least one notification in association with the individual.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this invention, illustrate various embodiments of the present invention. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present invention. This text is included for illustrative, non-limiting, explanatory purposes of certain embodiments detailed in the present invention.

DETAIL DESCRIPTIONS OF THE INVENTION

Figure 1:
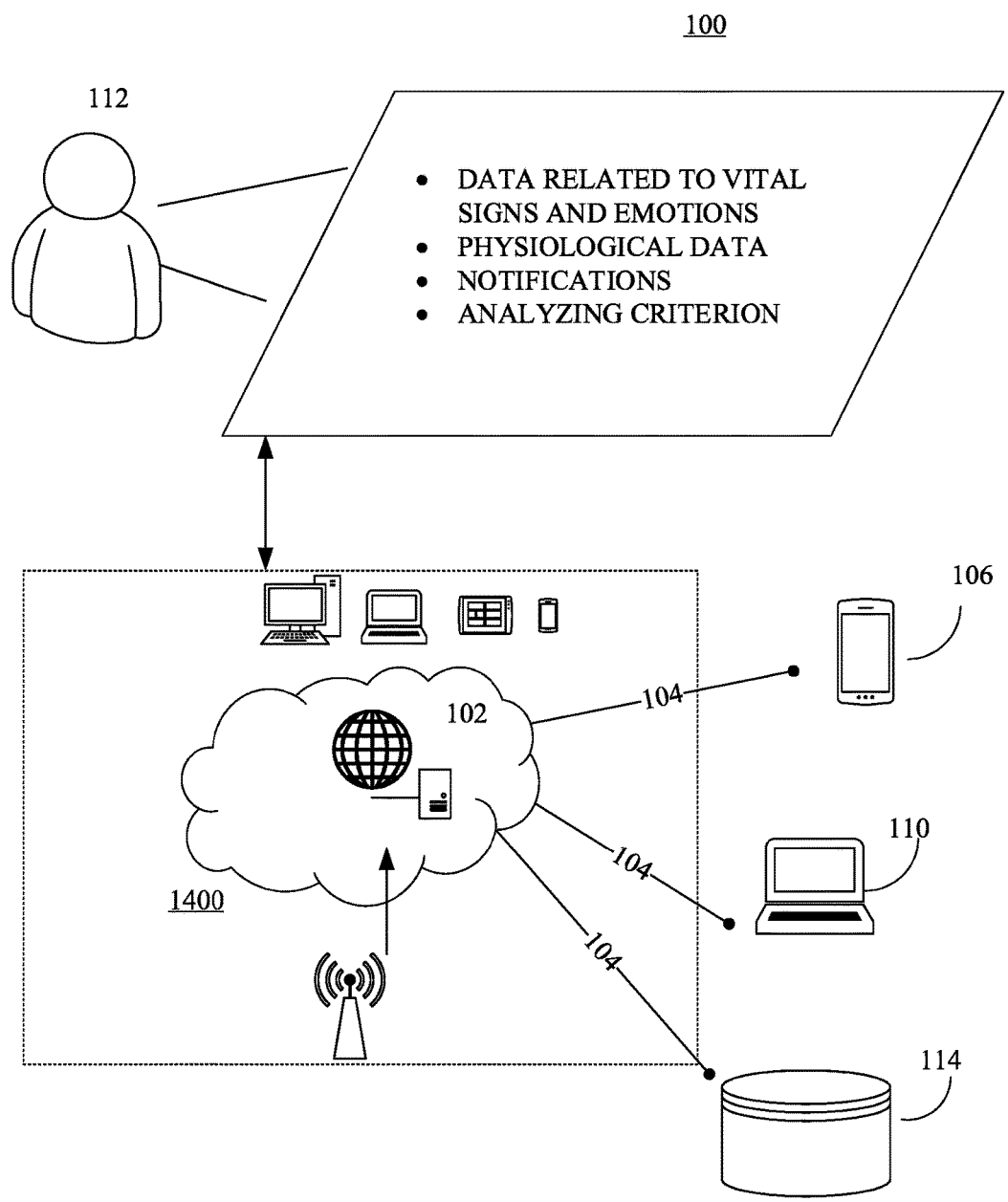
FIG. 1 is an illustration of an online platform consistent with various embodiments of the present invention.

As a preliminary matter, it will readily be understood by one having ordinary skill in the relevant art that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the embodiments of the present invention. Other embodiments also may be discussed for additional illustrative purposes in providing a full and enabling invention. Moreover, many embodiments, such as adaptations, variations, modifications, and equivalent arrangements, will be implicitly disclosed by the embodiments described herein and fall within the scope of the present invention.

Accordingly, while embodiments are described herein in detail in relation to one or more embodiments, it is to be understood that present invention is illustrative and exemplary of the present invention and are made merely for the purposes of providing a full and enabling invention. The detailed invention herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the invention may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the invention. Instead, the proper scope of the invention is defined by the appended claims. The present invention contains headers. It should be understood that these headers are used as references and are not to be construed as limiting upon the subjected matter disclosed under the header.

The present invention includes many aspects and features. Moreover, while many aspects and features relate to, and are described in the context of monitoring health of users, embodiments of the present invention are not limited to use only in this context.

According to some embodiments, a wearable device for monitoring of an individual is disclosed. The wearable device may be a smart bracelet or a smart watch, which may include a battery (such as a coin cell battery "CR2025" or a rechargeable battery), one or more sensors, a transceiver and a processing device. The one or more sensors may measure vital signs of the individual in real time. For example, the vital signs may include one or more of body temperature, pulse rate, respiratory rate, and blood pressure. The one or more sensors may be based on nanotechnology. The transceiver may be configured to send sensor data wirelessly to a smartphone. Further, the wearable device may include a button to manually trigger an alert. Further, the wearable device may detect the user's mood and track his/her emotions in real time. Further, the wearable device may be resistance to some depth under water. Further, the wearable device may include an adjustable wristband that will fit 99% of all wrists.

Further, the wearable device may include other smart features like measuring calories, counting steps (pedometer), an anti-theft feature, tracking of the daily routine and sleep time habits, and others. Further, as the user uses the wearable device for a period of time, and more data is collected, the wearable device may learn more about the user from the collected data and provide more accurate results.

Further, the wearable device may be configured to change its color, or an emoji face on its screen, depending on the mood of the user. The smartphone may wirelessly communicate with the wearable device. Further, the wearable device may detect the mood of the user automatically. The user may also select their mood manually on a mobile application on their smartphone. Further, the user may customize and decorate their wearable device by adding accessories and charms. Further, these accessories may include additional useful features for the user. For example, a charm may include a micro SD memory to save information, or a Bluetooth speaker, etc.

Further, the user may carry a smartphone with a mobile application. The smartphone may communicate with the wearable device to obtain data about the user. Further, there may be an API to facilitate the data transfer between the wearable device and the smartphone. Further, the smartphone may display the data received from the wearable device on the smartphone's screen. Accordingly, the user may be able to view the data (body temperature, pulse rate, respiratory rate, and blood pressure) received from the wearable device on the mobile application. Further, the mobile application may be able to update (in real time) a database in the cloud with all the user's data (such as body temperature, pulse rate, respiratory rate, and blood pressure), along with the user's location, provided by the smartphone's and/or wearable device's GPS, and information related to individual's mood. Further, the application may work directly with other smart watches.

According to further embodiments, the users with the disclosed wearable device and the disclosed mobile application installed on their smartphones may choose to follow other people (such as friends and family) to find out how they are and to track their vital signs in real time. They will be in the user's "Following" or "Watching" list. Therefore, the user may have other people (such as friends and family) following him/her to find out how the user is and to track his/her vital signs in real time. They will be the user's "Followers" or "Watchers" list. When the user receives a notification indicating that someone wants to follow him/her, the user may be able to accept or reject the request. This way the user may be more aware not only of the user's health but also of the health of his/her loved ones in real time. Further, the location of the user may be shared only if his/her vital signs fail or if the user wants to share the user's location with specific followers/watchers or with all of the user's followers/watchers, thereby allowing parents to have a tracking location device on their children all the time.

Further, the user will have the freedom to change the privacy of every feature at any time, and will be able to see the vital signs of the people the user is following, if the other person has this feature enabled on the privacy settings on the user's side, but if the other person has this feature like private, the user will only see that person's vital signs when and only if they ever fail. The user can select between sharing the user's vital signs and/or mood with no one, with specific followers/watchers, or with all of his/her followers/watchers. The same privacy settings options will be available for sharing the user's location and any other feature that may be considered as "needs to be private" at some point.

Further, the user's followers may react to his/her change of mood in the application by adding comments/pictures/etc. and encouraging him/her if the user feels depressed. The users may change their mood on the application even if they don't have the wearable device, by updating their status manually. This feature may help to prevent suicide by detecting if someone in the user's "Following/Watching" list is feeling sad and depressed and needs emotional support. Further, the disclosed application may provide similar features to the known social media applications.

According to an exemplary embodiment, in case the user's vital signs are falling in an abnormally low level or exceeding a normal level, the phone screen may show a notification asking the user if the user needs help or is in danger, giving to the user the options to choose between "No", if it is a false alarm, or "Yes" in case something is happening to him/her. The user may have a few seconds to answer this notification. In case the user doesn't answer, or has chosen the option "Yes", then an alert notification may be sent with his/her location and vital sign details to all the people who follow that user, to let them know that the user is in danger. This may be the default behavior of the application, but the user may choose what the application may do if any of his/her vital signs fail, by choosing between two options, including sending an alert notification with his/her location to all the people who follow him/her or call directly to an emergency telephone number (like 911), using a machine voice asking for help and saying his/her personal information and his/her location. The system may also send a text message to 911 in some areas where this service is available. Any other way of communication with the emergency number like automated API integrations between systems, etc. may be used to reach out to the emergency number as soon as possible.

Further, when a follower receives the alert notification on their smartphone and/or their wearable device, they are given two options. The first option is calling the user. If the user doesn't reply, then they may call the police and provide the location of the user in danger. The second option is calling the police directly and provide the location of the user in danger.

Finally, the follower who replied may mark the notification as "Help on its way" so the rest of the followers may know. On the other hand, if someone already replied to the alert notification before, then the rest of the followers may see this on their screens that someone already replied, and they may have to wait until the user who replied mark it as "Help on its way" or the user in danger marks himself/herself as safe. The rest of the followers may be able to see the name of the follower who replied the alert notification, only if that follower is on their follower and/or following list, and they may also call this follower back to get updates about the situation.

Further, the user may disable the wearable device via the mobile application if the user wishes. For example, the user may disable the wearable device when the user goes to an attractions park where the user knows that the user may have a high pulse rate all the time. The user may choose a specific period of time or reactivate it manually, but the mobile application after a certain time may send notifications to the user to reactivate the wearable device.

Custom algorithms will be used to handle some specific scenarios and avoid false alarms. For example, when checking the user's body temperature, the alert will be triggered only after a few minutes of sensing elevated temperature values, therefore if the user opens the oven just for a few seconds, and the wearable device receives high temperatures, this won't trigger the alert notification to the user's watchers/followers.

Further, the wearable device may also provide different ways to manually trigger the alert, like pressing a button, or touching the screen several times within a time period in an unusual way, for example, touching the screen more than 15 times in 10 seconds. Further, the wearable device may allow to manually trigger the alert via voice recognition, for example, the user may say a specific phrase like "I need help". Yet further, the wearable device may allow to manually trigger the alert via some specific wrist gestures, etc. This manual alert may be used when the user has no problems with his/her vital signs but is being assaulted on the street or is in a dangerous situation and wants to send an alert to his/her watchers/followers. Although, some conventional smart devices have the feature to send an alert to one of the user's contacts when a button is pressed several times. However, if the contact to whom the alert message is sent is not available at that specific moment, then the alert may go unnoticed. On the other hand, the disclosed system sends an alert to a bigger network of people (the watchers/followers of the user) which increases the chances that someone actually gets the alert. Further, the disclosed system may be configured to send the alert directly to the police department as well. Moreover, the alert notification may not be a simple text message, rather it may be like an amber alert, which produces a louder noise that is almost impossible to ignore by a listener. Further, the disclosed system provides the user with easier and faster options to trigger the alert from the wearable device, without having to take out the cellphone. Accordingly, the disclosed system provides more security to the user.

Further, when the user feels depressed, it isn't all in his/her head. Depression can disrupt sleep, instigate irregular eating and make him/her less active and social. It can completely disrupt his/her internal body clock and daily habits. The disclosed system will be monitoring his/her life habits, and if detects depression signs through custom algorithms, the user will get a notification in the smart phone and/or wearable device screen, asking if the user is feeling depressed, if the user confirms, then an alert will be triggered to his/her watchers, so they can provide emotional support to the user.

According to some embodiments, the disclosed devices, systems and methods may allow doctors to be aware of the vital signs of their patients in real time remotely.

According to some embodiments, the disclosed devices, systems and methods may allow people to keep an eye on their children or a senior relative who must be alone for some time.

According to some embodiments, the disclosed devices, systems and methods may allow people to keep an eye on the health of their family and friends, and be the first person to know if they are in danger.

According to some embodiments, the disclosed devices, systems and methods may allow a person who lives at home alone with health risks that if something happens to him/her no one would find out.

According to some embodiments, the disclosed devices, systems and methods may allow a person to ask for help in case the user is involved in a robbery, road accident or any other emergency situation, and there is no one around to help him/her.

According to some embodiments, the disclosed devices, systems and methods may allow people to be aware of their family and friends sentimental status, being able to provide emotional support in some cases like depression episodes.

FIG. 1 is an illustration of an online platform 100 consistent with various embodiments of the present invention. By way of non-limiting example, the online platform 100 for facilitating monitoring of an individual based on at least one wearable device may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114 (such as medical database etc.), over a communication network 104, such as, but not limited to, the Internet. Further, users of the online platform 100 may include relevant parties such as, but not limited to, end users, caregivers of end users, family members and friends of end users, and administrators. Accordingly, in some instances, electronic devices operated by the one or more relevant parties may be in communication with the platform 100.

A user 112, such as the one or more relevant parties, may access online platform 100 through a web-based software application or browser. The web-based software application may be embodied as, for example, but not be limited to, a website, a web application, a desktop application, and a mobile application compatible with a computing device 1400.

According to some embodiments, the online platform 100 may be configured to operate in conjunction with a system 200 for facilitating monitoring of an individual based on at least one wearable device. The system 200 is explained in detail below.

Figure 2:
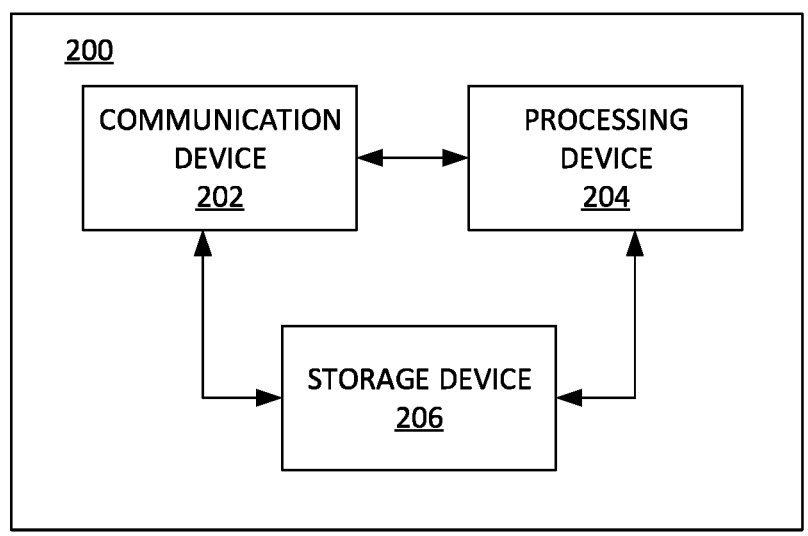
FIG. 2 is a block diagram of a system for facilitating the monitoring of an individual based on at least one wearable device, in accordance with various embodiments of the present invention.

FIG. 2 is a block diagram of the system 200 for facilitating the monitoring of an individual based on at least one wearable device, in accordance with various embodiments of the present invention. The system 200 may include a communication device 202 configured for receiving at least one physiological data from a user device associated with the individual. Further, the user device may be configured for receiving the at least one physiological data from at least one wearable device worn by the individual.

Figure 3:
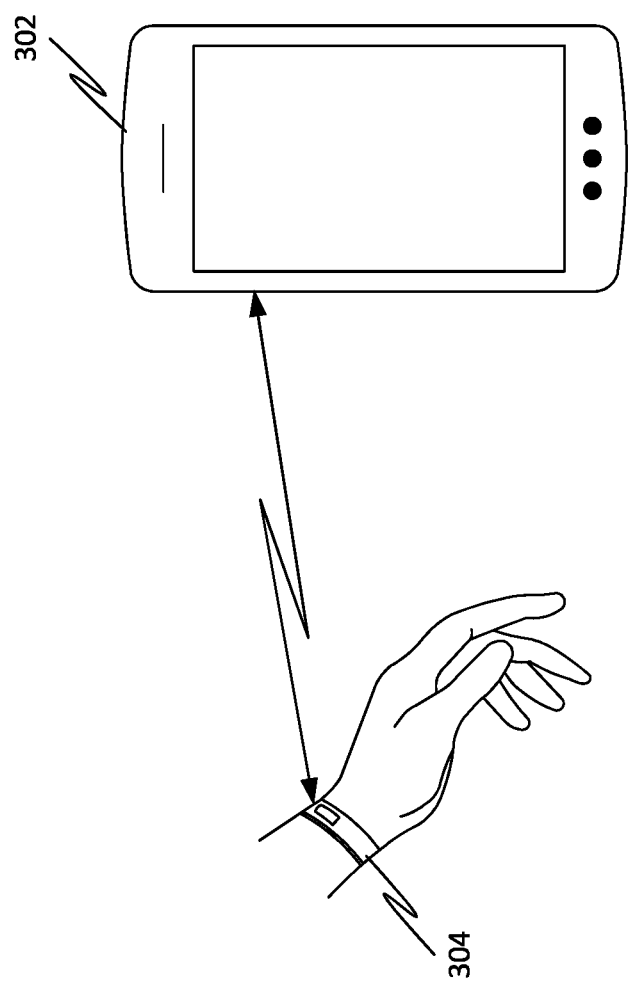
FIG. 3 illustrates a wearable device communicating with a smartphone, in accordance with various embodiments of the present invention.

As shown in FIG. 3, a smartphone 302 (the user's device) may be configured for receiving the at least one physiological data from at least one wearable device 304 worn by the user.

The wearable device 304 may be a smart bracelet or a smart watch and may include a battery (such as a coin cell battery "CR2025" or a rechargeable battery), one or more sensors, a transceiver, and a processing device. The one or more sensors may measure vital signs in real time. For example, the vital signs may include one or more of body temperature, pulse rate, respiratory rate, and blood pressure. The one or more sensors may be based on nanotechnology. The transceiver may be configured to send sensor data wirelessly to the smartphone 302. Further, the wearable device 304 may include a button to manually trigger the alert. Further, the wearable device 304 may detect the user's mood and keep tracking of his/her emotions in real time. Further, the wearable device 304 may be resistance to some depth under water. Further, the wearable device 304 may include an adjustable wristband that will fit 99% of all wrists.

The smartphone 302 may include an application that may allow the individual to check the health data (such as body temperature, pulse rate, respiratory rate, and blood pressure) received from the wearable device 304. The application may be able to update in real time a database in the cloud with all the health data, along with the individual's location (provided by the smartphone's and/or wearable device's GPS) and information related to individual's mood. Further, the application may be installed on smartwatches.

Further, in some embodiments, the user device may include the at least one wearable device.

Further, the at least one wearable device may include at least one physiological sensor configured for generating the at least one physiological data. Further, the at least one physiological data may be associated with a user identifier of the individual. Further, the communication device 202 may be configured for transmitting at least one notification to at least one watcher device associated with at least one watcher identifier. For example, at least one watcher device may be an electronic communication device of a caregiver (such as a doctor, a nurse etc.) or a family member of the individual.

Further, the system 200 may include a processing device 204 configured for analyzing the at least one physiological data based on at least one analyzing criterion. In general, an analyzing criterion may capture a state of the individual of interest. In some embodiments, the state may include a physiological state. For example, the analyzing criterion may indicate an acceptable value and/or range corresponding to one or more physiological variables such as, but not limited to, heart rate, respiratory rate, Galvanic Skin Resistance (GSR), blood pressure, insulin level, EMG, EEG and so on. In some embodiments, the state may include an emotional state. Accordingly, the at least one analyzing criterion may indicate one or more emotional state such as stress, anger, depression, anxiety and so on. Accordingly, physiological correlates (including corresponding values and/or ranges) of the one or more emotional state may be identified. For example, a specification of anger in the analyzing criterion may be used to automatically identify relevant physiological correlates such as increased heart rate, increased perspiration (As reflected in lowered GSR values), changes in EMG/EEG waves and so on. Further, the processing device 204 may be configured for generating at least one notification based on the analyzing. Accordingly, in an example, when the individual is exhibiting symptoms of depression, the at least one notification may be generated when the at least one physiological data is found to be within the ranges of physiological correlates of depression, and if the user confirms his/her depression status on the notification, then another notification may be send to his/her followers/watchers, so they can provide emotional support to the user.

Further, the system 200 may include a storage device 206 configured for retrieving the at least one analyzing criterion based on the user identifier. Further, the storage device 206 may be configured for retrieving the at least one watcher identifier based on the user identifier. Further, the at least one watcher identifier may be associated with at least one watcher registered to receive the at least one notification in association with the individual.

In some embodiments, the communication device 202 may be further configured for receiving at least one response from one or more of the user devices and the at least one watcher device. Further, the at least one response corresponds to the at least one notification. Further, the processing device 204 may be further configured for performing machine learning on each of the at least one physiological data, the at least one notification and the at least one response in association with the user identifier. Further, the processing device 204 may be configured for generating the at least one analyzing criterion based on the machine learning. Further, the storage device 206 may be further configured for storing the at least one analyzing criterion.

In some embodiments, the storage device 206 may be further configured for storing a first physiological data corresponding to a first time period. Further, the processing device 204 may be further configured for analyzing the first physiological data. Further, the processing device 204 may be configured for generating a user model based on the analyzing of the first physiological data. Further, the processing device 204 may be configured for predicting a second physiological data corresponding to a second time period based on the user model. Further, the at least one analyzing criterion may be based on the second physiological data.

In some embodiments, the communication device 202 may be further configured for receiving medical data of the individual from at least one clinical database associated with the individual. Further, the processing device 204 may be further configured for analyzing the medical data. Further, the processing device 204 may be configured for generating the at least one analyzing criterion based on the analyzing of the medical data.

In some embodiments, the communication device 202 may be further configured for receiving a first analyzing criterion from a first watcher device. Further, the communication device 202 may be configured for receiving a second analyzing criterion from a second watcher device. Further, the at least one analyzing criterion may include the first analyzing criterion and the second analyzing criterion. Further, the at least one notification may include a first notification and a second notification. Further, the communication device 202 may be configured for transmitting the first notification to the first watcher device. Further, the communication device 202 may be configured for transmitting the second notification to the second watcher device. Accordingly, in some embodiments, different watchers may specify different analyzing criterion. For example, a physician may specify, through a physician device, the first analyzing criterion comprising acceptable ranges of vital parameters such as heart-rate, breathing and blood pressure in relation to the individual wearing the wearable device 304. Accordingly, the online platform may analyze the at least one physiological data in order to determine whether any anomaly exists regarding the vital parameters specified in the first analyzing criterion. Subsequently, if the at least one physiological data is found to be anomalous, a first notification may be generated and transmitted to the physician device. As a result, the physician may be able to keep track of physiological parameters of interest to the physician. On the other hand, a family member of the individual may specify the second analyzing criterion including acceptable ranges of physiological parameters that may not necessarily limited to vital parameters. For example, the second analyzing criterion may include indication of an acceptable range of perspiration levels (as determined by a galvanic skin resistance (GSR) sensor). For example, a family member of the individual may be interested to know when the individual is under stress (as exhibited in changes in GSR values). Accordingly, the online platform may analyze the at least one physiological data and generate a second notification in case an anomalous GSR value is detected. Subsequently, the second notification may be transmitted to the second watcher device associated with the family member. As a result, the family member may be able to track a physiological parameter of interest to the family member.

In some embodiments, the one or more of the at least one wearable device and the user device may include a location sensor. Further, the communication device 202 may be further configured for receiving location data corresponding to the individual. Further, the at least one notification further may include the location data.

In some embodiments, the at least one watcher device may include a first watcher device and a second watcher device. Further, the communication device 202 may be further configured for receiving a first response indication of a first response from the first watcher device. Further, the first response corresponds to the at least one notification. Further, the communication device 202 may be configured for transmitting the first response indication to the second watcher device.

In some embodiments, the communication device 202 may be further configured for receiving one or more of motion data and environmental data from one or more of the user devices and the at least one wearable device including one or more of a motion data sensor and an environmental sensor. Further, the generating of the at least one notification may be further based on one or more of the motion data and the environmental data. Further, the at least one notification further may include one or more of the motion data and the environmental data.

In some embodiments, the communication device 202 may be further configured for transmitting the at least one notification to the at least one wearable device. Further, the at least one wearable device may include a pill dispenser configured for dispensing at least one pill based on the at least one notification. In another embodiment, the pill dispenser may be a small box separated from the wearable device. The user may carry the pill dispenser in their pocket. Further, the pill dispenser may be connected to the wearable device or to the smart-phone directly. This is explained in further detail in conjunction with FIG. 4 below.

Figure 4:
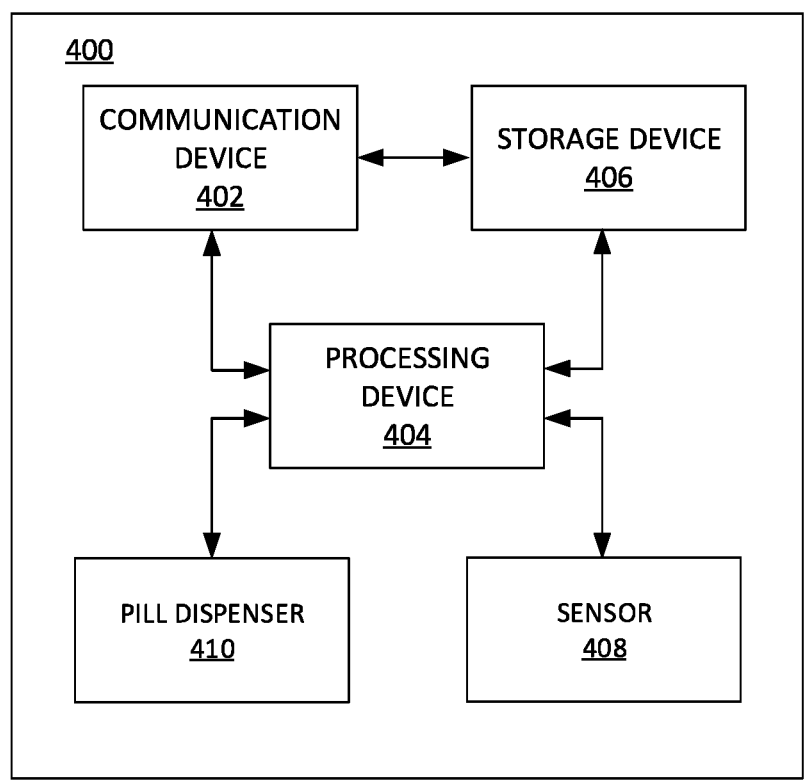
FIG. 4 is a block diagram of a wearable device for monitoring a user, in accordance with various embodiments of the present invention.

FIG. 4 is a block diagram of a wearable device 400 for monitoring an individual, in accordance with various embodiments of the present invention. The wearable device 400 may include a communication device 402, a processing device 404, a storage device 406, one or more sensors 408 and a pill dispenser 410. The one or more sensors 408 may include one or more of at least one physiological sensor configured for generating the at least one physiological data, a location sensor, a motion data sensor and an environmental sensor. The pill dispenser 410 may include a small container with a lid. The small container may store one or more pills such as lifesaving drugs. For example, a notification may be received by the communication device 402, which may be processed by the processing device 404 in conjunction with instructions stored in the storage device 406. Thereafter, the processing device 404 may send a signal to electronically open the lid such that the individual may access the one or more pills stored in the small container. Further, the processing device 404 may keep a record in the storage device 406 each time the pill dispenser is opened, so the user can have a history log of the pills the user has taken.

Figure 5:
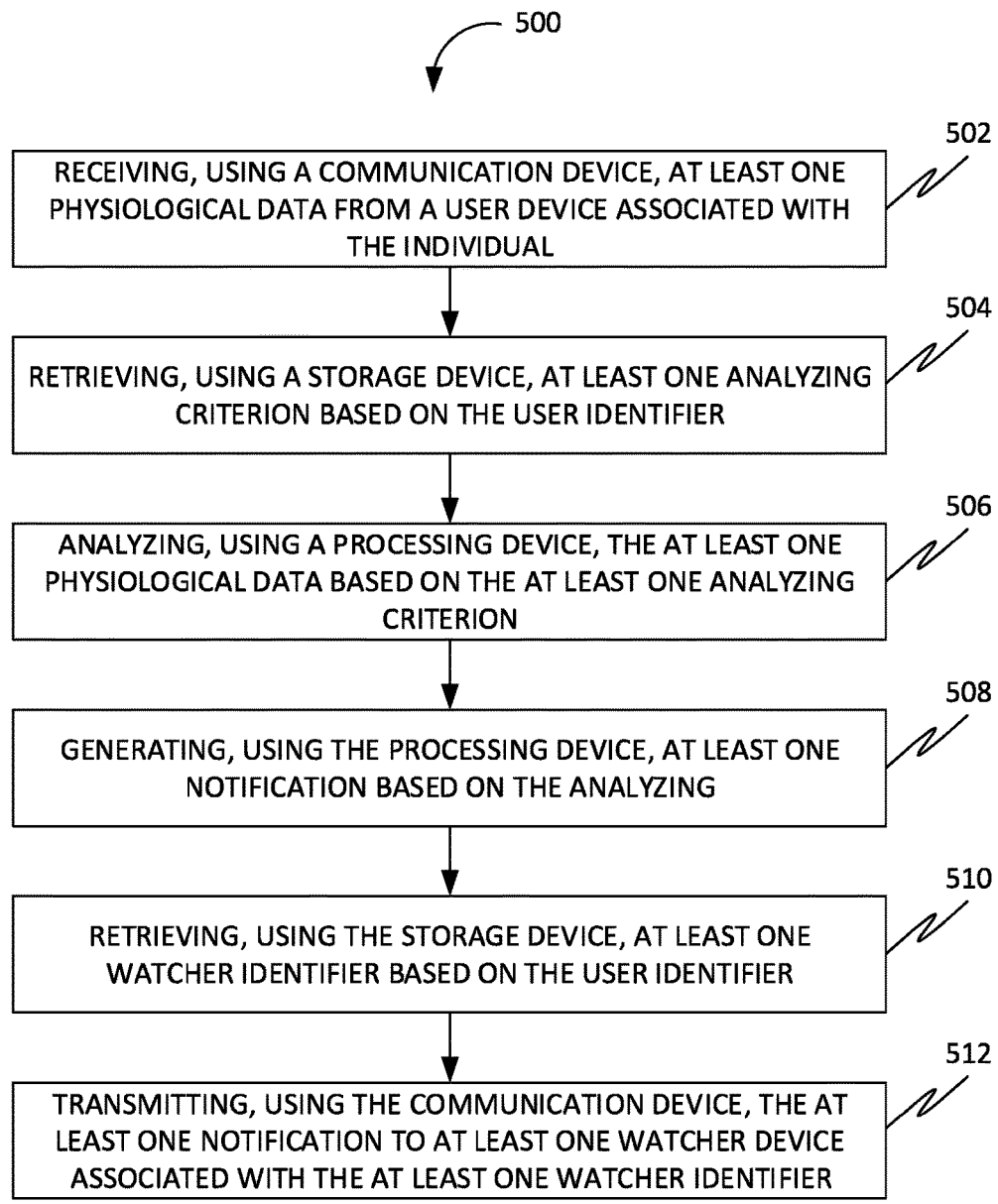
FIG. 5 is a flowchart of a method of facilitating the monitoring of an individual based on at least one wearable device, in accordance with an exemplary embodiment.

FIG. 5 is a flowchart of a method 500 of facilitating monitoring of an individual based on at least one wearable device, in accordance with an exemplary embodiment. At 502, the method 500 may include receiving, using a communication device (such as the communication device 202), at least one physiological data from a user device associated with the individual. In some embodiments, the user device may include the at least one wearable device. Further, the user device may be configured for receiving the at least one physiological data from at least one wearable device worn by the individual. Further, the at least one wearable device may include at least one physiological sensor configured for generating the at least one physiological data. Further, the at least one physiological data may be associated with a user identifier of the individual.

Further, at 504, the method 500 may include retrieving, using a storage device (such as the storage device 206), at least one analyzing criterion based on the user identifier. Further, at 506, the method 500 may include analyzing, using a processing device (such as the processing device 204), the at least one physiological data based on the at least one analyzing criterion.

Further, at 508, the method 500 may include generating, using the processing device, at least one notification based on the analyzing.

Further, at 510, the method 500 may include retrieving, using the storage device, at least one watcher identifier based on the user identifier. Further, the at least one watcher identifier may be associated with at least one watcher registered to receive the at least one notification in association with the individual. Further, at 512, the method may include transmitting, using the communication device, the at least one notification to at least one watcher device associated with the at least one watcher identifier.

In further embodiments, the one or more of the at least one wearable device and the user device may include a location sensor. Accordingly, the method 500 may also include receiving, using the communication device, location data corresponding to the individual. Further, the at least one notification further may include the location data.

In further embodiments, the method 500 may further include receiving, using the communication device, one or more of motion data and environmental data from one or more of the user device and the at least one wearable device including one or more of a motion data sensor and an environmental sensor. Further, the generating of the at least one notification may be further based on one or more of the motion data and the environmental data. Further, the at least one notification further may include one or more of the motion data and the environmental data.

In further embodiments, the method 500 may further include transmitting the at least one notification to the at least one wearable device. Further, the at least one wearable device may include a pill dispenser configured for dispensing at least one pill based on the at least one notification. The pill dispenser has been explained in detail in conjunction with FIG. 4 above.

Figure 6:
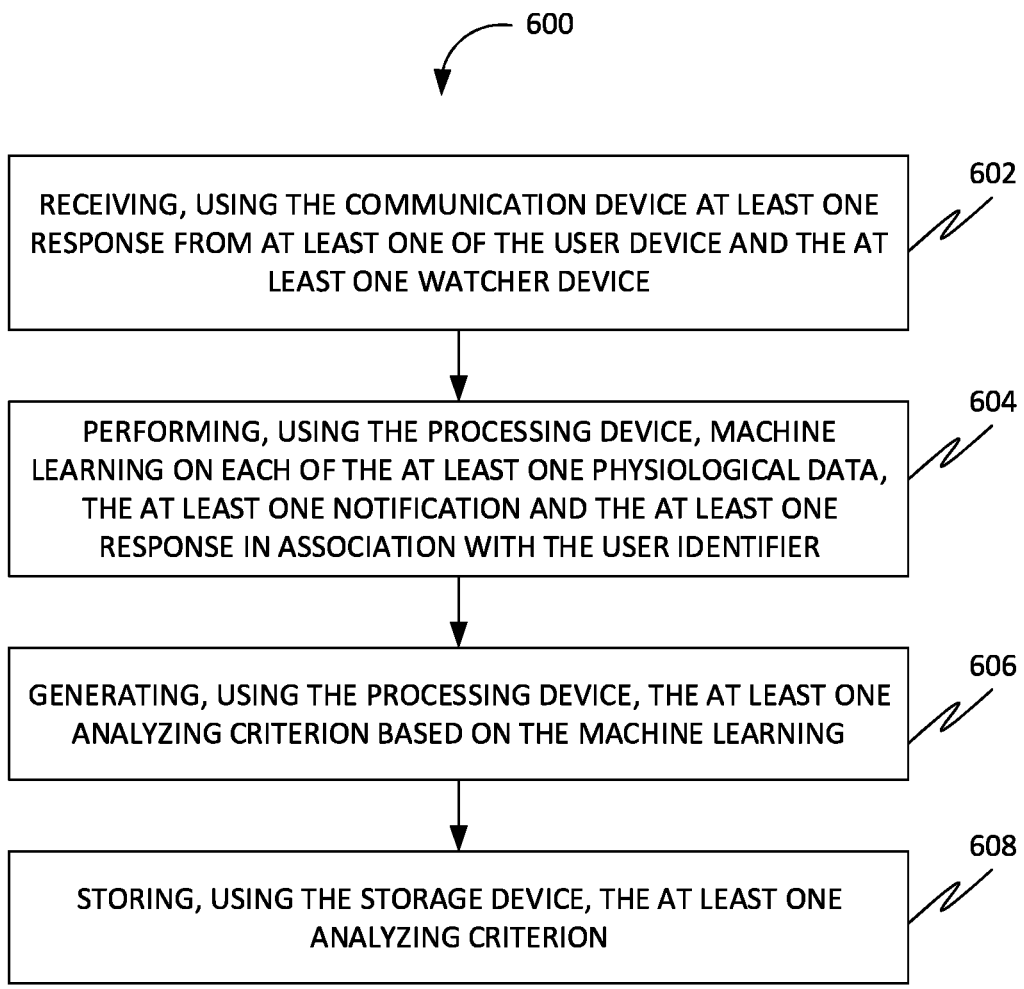
FIG. 6 is a flowchart of a method of producing an at least one analyzing criterion, in accordance with further embodiments.

FIG. 6 is a flowchart of a method 600 of producing the at least one analyzing criterion, in accordance with further embodiments. At 602, the method 600 may include receiving, using the communication device at least one response from one or more of the user devices and the at least one watcher device. Further, the at least one response corresponds to the at least one notification.

Further, at 604, the method 600 may include performing, using the processing device, machine learning on each of the at least one physiological data, the at least one notification and the at least one response in association with the user identifier. Then, at 606, the method 600 may include generating, using the processing device, the at least one analyzing criterion based on the machine learning. At 608, the method 600 may include storing, using the storage device, the at least one analyzing criterion.

Figure 7:
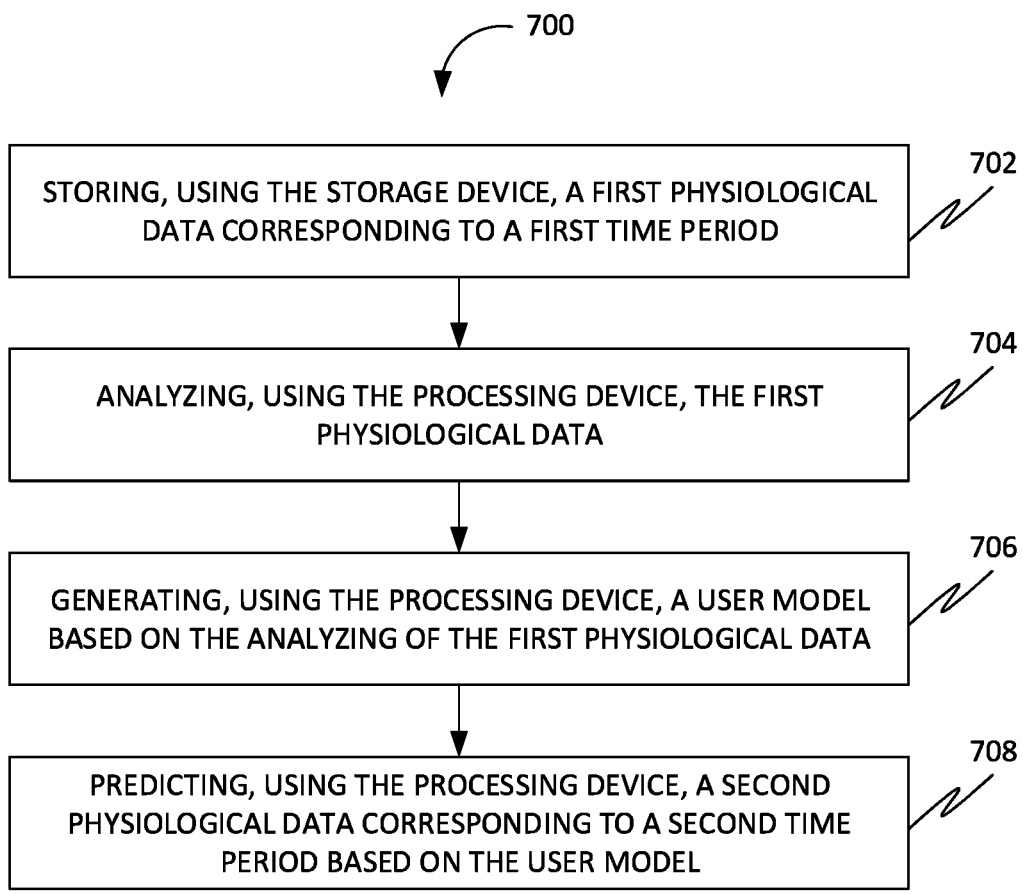
FIG. 7 is a flowchart of a method of obtaining a user model, in accordance with further embodiments.

FIG. 7 is a flowchart of a method 700 of obtaining a user model, in accordance with further embodiments. At 702, the method 700 may include storing, using the storage device, a first physiological data corresponding to a first time period. Further, at 704, the method 700 may include analyzing, using the processing device, the first physiological data. Further, at 706, the method 700 may include generating, using the processing device, a user model based on the analyzing of the first physiological data. Further, at 708, the method 700 may include predicting, using the processing device, a second physiological data corresponding to a second time period based on the user model. Further, the at least one analyzing criterion may be based on the second physiological data.

Figure 8:
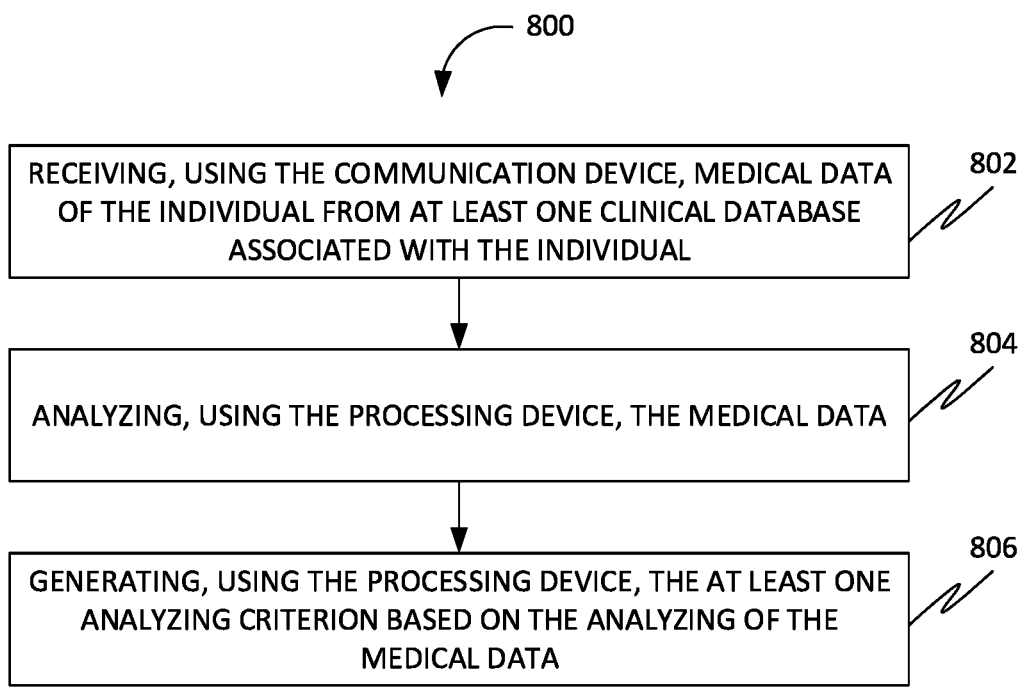
FIG. 8 is a flowchart of a method of obtaining an at least one analyzing criterion based on medical data associated with the user, in accordance with further embodiments.

FIG. 8 is a flowchart of a method 800 of obtaining the at least one analyzing criterion based on medical data associated with the individual, in accordance with further embodiments. At 802, the method 800 may include receiving, using the communication device, medical data of the individual from at least one clinical database associated with the individual.

Further, at 804, the method 800 may include analyzing, using the processing device, the medical data. Further, at 806, the method 800 may include generating, using the processing device, the at least one analyzing criterion based on the analyzing of the medical data.

Figure 9:
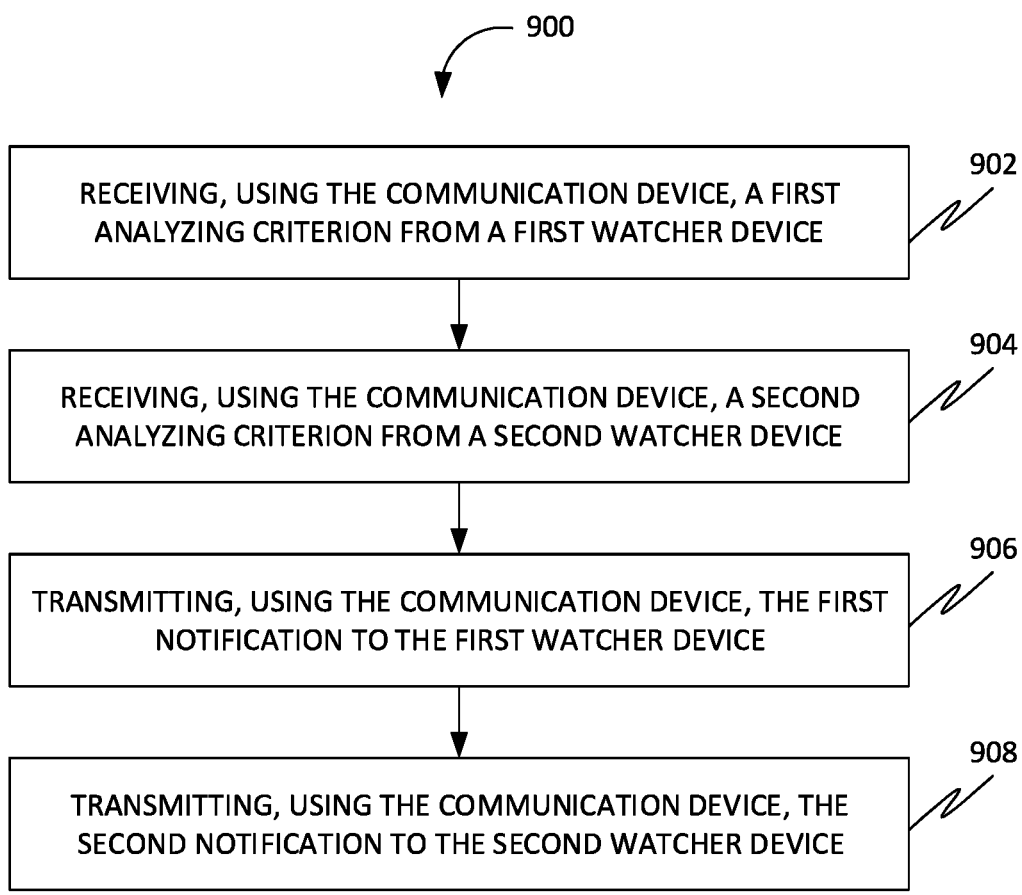
FIG. 9 is a flowchart of a method of customizing notifications based on an analyzing criterion provided by an individual, in accordance with further embodiments.

FIG. 9 is a flowchart of a method 900 of customizing notifications based on an analyzing criterion provided by an individual, in accordance with further embodiments. At 902, the method 900 may include receiving, using the communication device, a first analyzing criterion from a first watcher device.

Further, at 904, the method 900 may include receiving, using the communication device, a second analyzing criterion from a second watcher device. Further, the at least one analyzing criterion may include the first analyzing criterion and the second analyzing criterion. Further, the at least one notification may include a first notification and a second notification.

At 906, the method 900 may include transmitting, using the communication device, the first notification to the first watcher device. Further, at 908, the method 900 may include transmitting, using the communication device, the second notification to the second watcher device.

Figure 10:
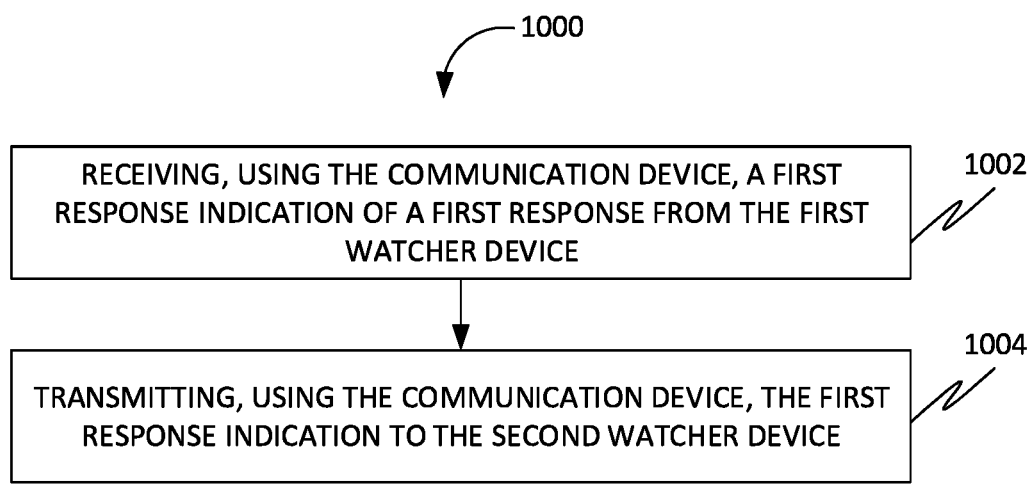
FIG. 10 is a flowchart of a method of facilitating communication between one or more watchers, in accordance with an exemplary embodiment.

FIG. 10 is a flowchart of a method 1000 of facilitating communication between one or more watchers, in accordance with an exemplary embodiment. In some embodiments, the at least one watcher device may include a first watcher device and a second watcher device. At 1002, the method 1000 may include receiving, using the communication device, a first response indication of a first response from the first watcher device. Further, the first response corresponds to the at least one notification. Further, at 1004, the method 1000 may include transmitting, using the communication device, the first response indication to the second watcher device.

Figure 11:
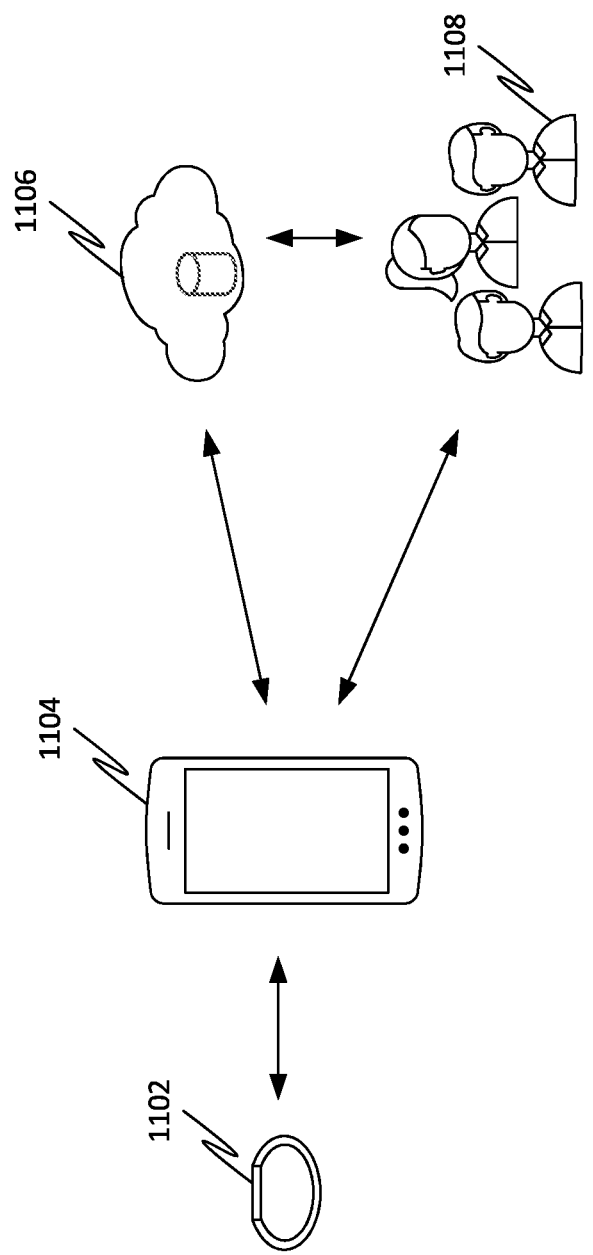
FIG. 11 illustrates the flow of information in accordance with an exemplary embodiment.

FIG. 11 illustrates flow of information in accordance with an exemplary embodiment. A user may wear a wearable device 1102. The wearable device 1102 may be configured to measure vital signs (health data) of the user in real time. Thereafter, the wearable device 1102 may transmit the health data to a smartphone 1104 of the user. A mobile application installed on the smartphone 1104 may display the health data for the user. Further, the smartphone 1104 may transmit the health data to a cloud 1106 (such as the centralized server 102). Thereafter, the mobile application in the smartphone 1104 connected to the cloud 1106 may send notifications (when required) to one or more watchers (or followers) 1108. This is explained in further detail in conjunction with FIG. 12 below.

Further, the mobile application on the smartphone 1104 may receive the data from the wearable device 1102, add it periodically to a database (such as the cloud 1106), to keep a log, and to learn about the user in order to provide more accurate results. For example, the mobile application may receive the data from the wearable device 1102 every a certain time period. Thereafter, if the mobile application on the smartphone 1104 gets anomalies on the health/emotions values from the wearable device 1102 (like blood pressure too high), or the user triggered the alert manually, the mobile application obtains the already stored data from the database, analyzes the values obtained from the wearable device 1102 and if it's considered an alert, then the mobile application sends the alert to the watchers 1108, and when these alerts are sent, a record for each alert is also stored on the database, like a log. Further, when a watcher responds to the alert, the record for that alert on the database is updated. The mobile application may get the data from the database and in response the mobile application may update the notification on the screen saying that someone already answered to the alert and updating the rest of the followers/watchers who got that alert.

Figure 12:
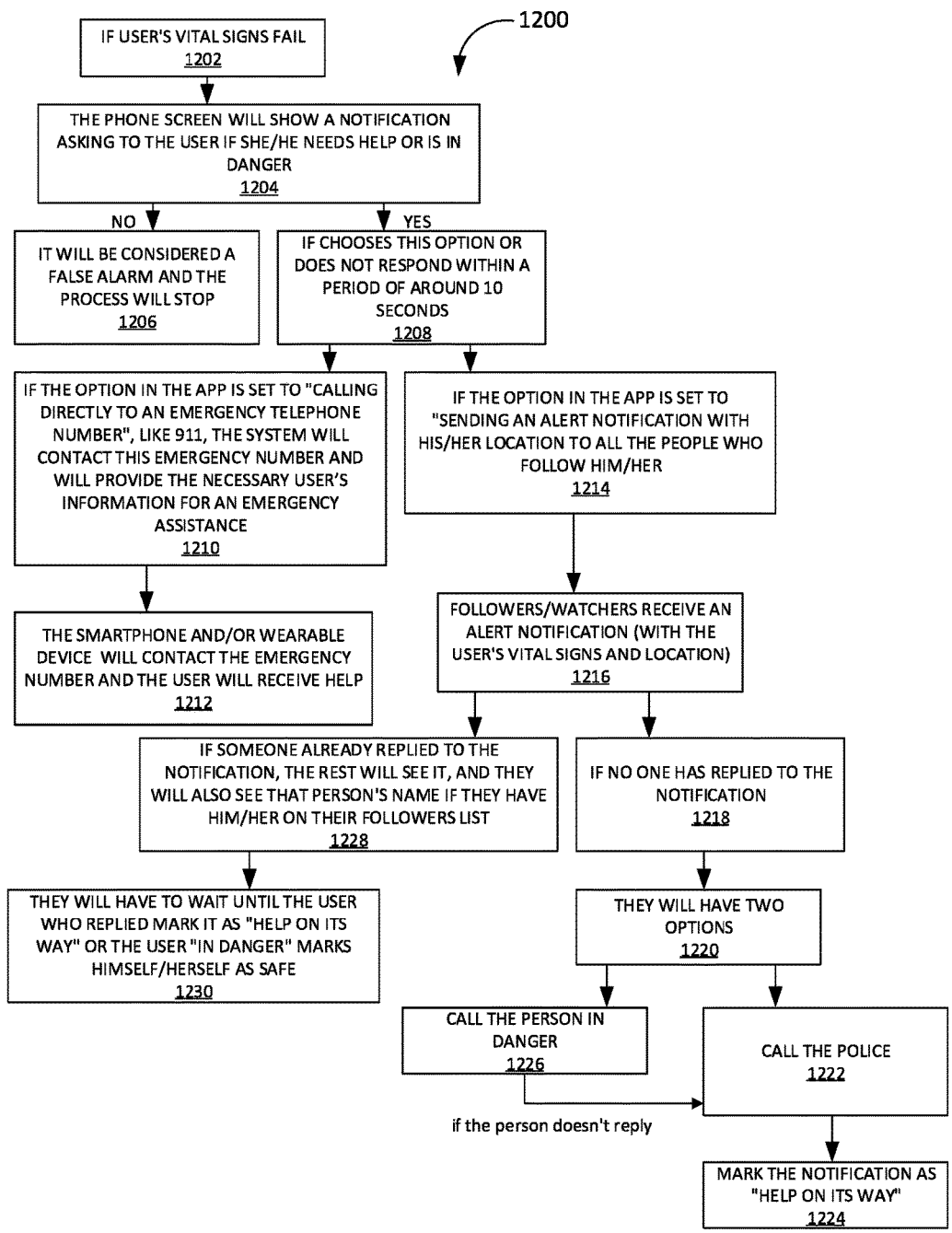
FIG. 12 is a flowchart of a method of facilitating the monitoring of an individual based on the wearable device, in accordance with an exemplary embodiment.

FIG. 12 is a flowchart of a method 1200 of facilitating monitoring of an individual based on the wearable device 1102, in accordance with an exemplary embodiment. At 1202, the method 1200 may include one or both of the wearable device 1102 and the smartphone 1104 detecting failure of vital signs of the user. In response, at 1204, the method 1200 may include the smartphone 1104 displaying a notification asking the user, if the user needs help or if the user is in danger. If the user indicates that the user is not in danger, then, at 1206, the method 1200 may include reporting the alarm as a false alarm.

However, at 1208, if the user indicates that the user is in danger or the user does not respond within a specific time period (such as 10 seconds), then, the mobile application performs actions based on predetermined settings.

At 1210, the method 1200 may determine the setting to be: call directly to an emergency telephone number (like 911) the system will contact this emergency number and will provide the necessary user's information for an emergency assistance. Accordingly, at 1212, the user's phone (the smartphone 1104) and/or the wearable device 1102 will contact the emergency number and the user will receive help.

However, at 1214, the method 1200 may determine the setting to be: send an alert notification with his/her location to all the people who follow him/her. Accordingly, at 1216, the method 1200 may include the followers/watchers receiving an alert notification (with the user's vital signs and location). Then, a follower/watcher may try to reach the user. However, at 1218, if no one has replied to the notification, then the followers/watchers may be provided two options at 1220. Accordingly, at 1222, the user may call the police and mark a notification as "help on its way" at 1224. Alternatively, the follower/watcher may call the user in danger at 1226. If the user does not reply, then the user may call the police at 1222.

Meanwhile, at 1228, if someone already replied to the notification, the remaining followers/watchers may see it, and they may see that person's name if they have him/her on their followers' list. Thereafter, at 1230, they may wait until the follower/watcher who replied mark it as "help on its way" or the user "in danger" marks himself/herself as safe.

Figure 13:
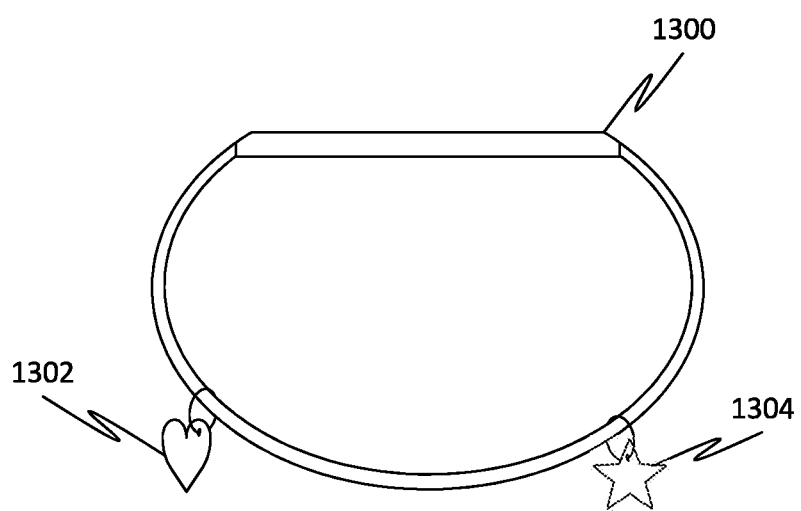
FIG. 13 is a wearable device for monitoring an individual, in accordance with an exemplary embodiment.

FIG. 13 is a wearable device 1300 for monitoring an individual, in accordance with an exemplary embodiment. The wearable device 1300 may be a smart bracelet or smart watch that may change its color, or have an emoji face on its screen, depending on the mood of the user wearing the wearable device 1300. The smartphone may wirelessly communicate with the wearable device 1300. Further, the wearable device 1300 may detect the mood of the user automatically. The user may also select his/her mood manually on a mobile application on their smartphone.

Further, the user may customize and decorate the wearable device 1300 by adding accessories and charms 1302-1304. Further, the accessories and the charms 1302-1304 may include useful features. For example, the charms 1302-1304 may include a micro SD memory to save information or a Bluetooth speaker etc.

Figure 14:
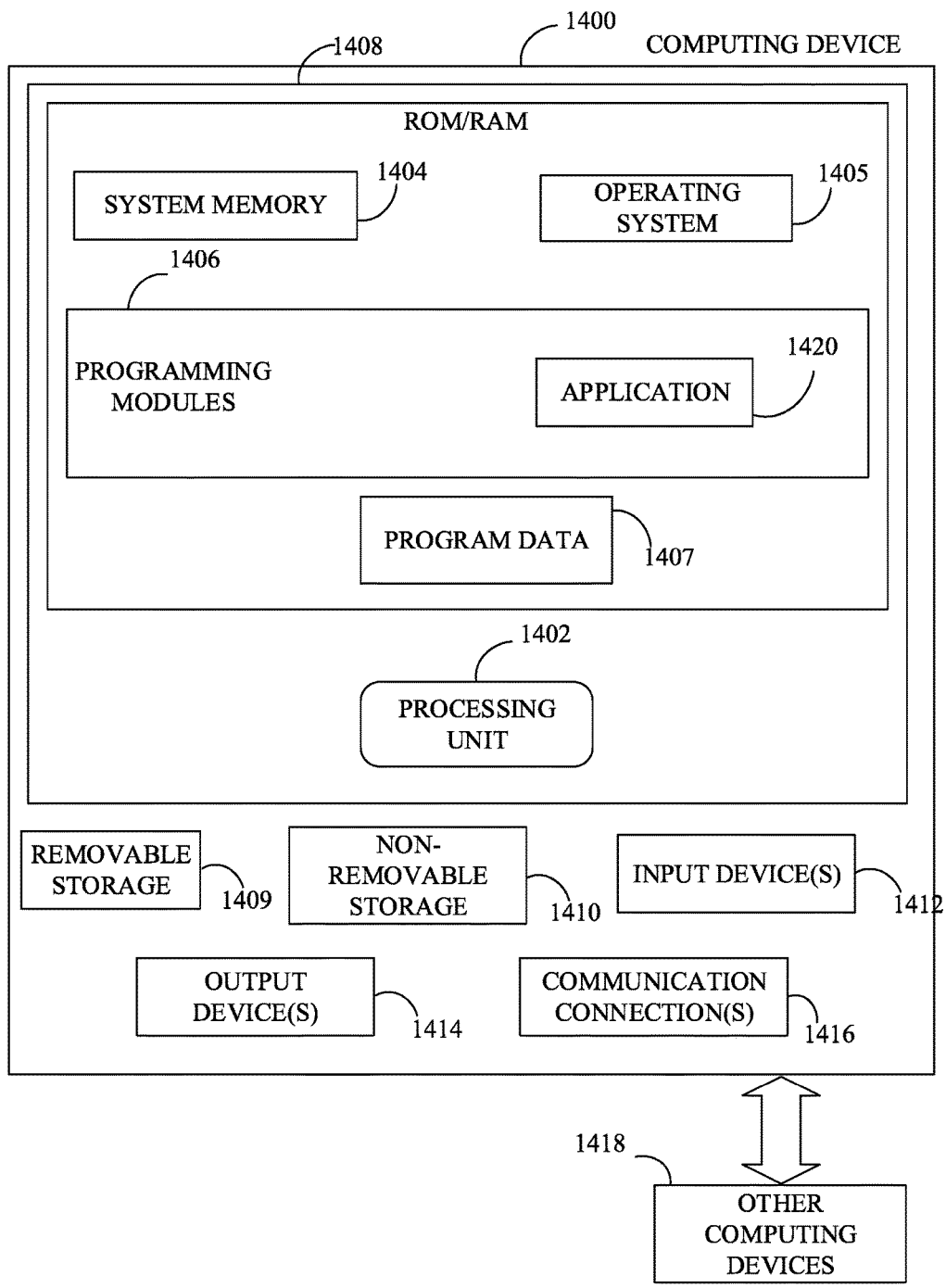
FIG. 14 is a block diagram of a computing device for implementing the methods of the present invention disclosed herein, in accordance with some embodiments.

With reference to FIG. 14, a system consistent with an embodiment of the invention may include a computing device or cloud service, such as computing device 1400. In a basic configuration, computing device 1400 may include at least one processing unit 1402 and a system memory 1404. Depending on the configuration and type of computing device, system memory 1404 may comprise, but is not limited to, volatile (e.g. random-access memory (RAM)), non-volatile (e.g. read-only memory (ROM)), flash memory, or any combination. System memory 1404 may include operating system 1405, one or more programming modules 1406, and may include a program data 1407. Operating system 1405, for example, may be suitable for controlling computing device 1400's operation. In one embodiment, programming modules 1406 may include a machine learning module. Furthermore, embodiments of the invention may be practiced in conjunction with a graphics library, other operating systems, or any other application program and is not limited to any particular application or system. This basic configuration is illustrated in FIG. 14 by those components within a dashed line 1408.

Computing device 1400 may have additional features or functionality. For example, computing device 1400 may also include additional data storage devices (removable and/or non-removable) such as, for example, magnetic disks, optical disks, or tape. Such additional storage is illustrated in FIG. 14 by a removable storage 1409 and a non-removable storage 1410. Computer storage media may include volatile and nonvolatile, removable and non-removable media implemented in any method or technology for storage of information, such as computer-readable instructions, data structures, program modules, or other data. System memory 1404, removable storage 1409, and non-removable storage 1410 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1400. Any such computer storage media may be part of device 1400. Computing device 1400 may also have input device(s) 1412 such as a keyboard, a mouse, a pen, a sound input device, a touch input device, a location sensor, a camera, a biometric sensor, etc. Output device(s) 1414 such as a display, speakers, a printer, etc. may also be included. The aforementioned devices are examples and others may be used.

Computing device 1400 may also contain a communication connection 1416 that may allow device 1400 to communicate with other computing devices 1418, such as over a network in a distributed computing environment, for example, an intranet or the Internet. Communication connection 1416 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1404, including operating system 1405. While executing on processing unit 1402, programming modules 1406 (e.g., application 1420 such as a media player) may perform processes including, for example, one or more stages of methods 500-1000 and 1200, algorithms, systems, applications, servers, databases as described above. The aforementioned process is an example, and processing unit 1402 may perform other processes. Other programming modules that may be used in accordance with embodiments of the present invention may include machine learning application etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present invention may be embodied in hardware and/or in software (including firmware, resident software, micro-code, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the invention.

Although the invention has been explained in relation to its preferred embodiment, it is to be understood that many other possible modifications and variations can be made without departing from the spirit and scope of the invention.

I claim:

1. A method of facilitating monitoring of an individual based on at least one wearable device, the method comprising:

receiving, using a communication device, at least one physiological data from a user device associated with the individual, wherein the user device is configured for receiving the at least one physiological data from at least one wearable device worn by the individual, wherein the at least one wearable device comprises at least one physiological sensor configured for generating the at least one physiological data, wherein the at least one physiological data is associated with a user identifier of the individual;

retrieving, using a storage device, at least one analyzing criterion based on the user identifier;

analyzing, using a processing device, the at least one physiological data based on the at least one analyzing criterion;

generating, using the processing device, at least one notification based on the analyzing;

retrieving, using the storage device, at least one watcher identifier based on the user identifier, wherein the at least one watcher identifier is associated with at least one watcher registered to receive the at least one notification in association with the individual;

transmitting, using the communication device, the at least one notification to at least one watcher device associated with the at least one watcher identifier;

receiving, using the communication device, at least one response from at least one of the user device and the at least one watcher device, wherein the at least one response corresponds to the at least one notification;

performing, using the processing device, machine learning on each of the at least one physiological data, the at least one notification and the at least one response in association with the user identifier;

generating, using the processing device, the at least one analyzing criterion based on the machine learning;

storing, using the storage device, the at least one analyzing criterion; and storing, using the storage device, a first physiological data corresponding to a first time period;

analyzing, using the processing device, the first physiological data;

generating, using the processing device, a user model based on the analyzing of the first physiological data;

predicting, using the processing device, a second physiological data corresponding to a second time period based on the user model, wherein the at least one analyzing criterion is based on the second physiological data;

receiving, using the communication device, location data corresponding to the individual, wherein the at least one notification further comprises the location data, and wherein the at least one of the at least one wearable device and the user device comprises a location sensor; and transmitting the at least one notification to the at least one wearable device, wherein the at least one wearable device is communicatively coupled to a pill dispenser configured for dispensing at least one pill based on the at least one notification.

2. The method of claim 1, wherein the user device comprises the at least one wearable device.

3. The method of claim 1 further comprising:

receiving, using the communication device, medical data of the individual from at least one clinical database associated with the individual;

analyzing, using the processing device, the medical data; and generating, using the processing device, the at least one analyzing criterion based on the analyzing of the medical data.

4. The method of claim 1 further comprising:
receiving, using the communication device, a first analyzing criterion from a first watcher device;
receiving, using the communication device, a second analyzing criterion from a second watcher device, wherein the at least one analyzing criterion comprises the first analyzing criterion and the second analyzing criterion, wherein the at least one notification comprises a first notification and a second notification;
transmitting, using the communication device, the first notification to the first watcher device; and
transmitting, using the communication device, the second notification to the second watcher device.

5. The method of claim 1, wherein the at least one watcher device comprises a first watcher device and a second watcher device, wherein the method further comprises:
receiving, using the communication device, a first response indication of a first response from the first watcher device, wherein the first response corresponds to the at least one notification; and
transmitting, using the communication device, the first response indication to the second watcher device.

6. The method of claim 1 further comprising receiving, using the communication device, at least one of motion data and environmental data from at least one of the user device and the at least one wearable device comprising at least one of a motion data sensor and an environmental sensor, wherein the generating of the at least one notification is further based on at least one of the motion data and the environmental data, wherein the at least one notification further comprises at least one of the motion data and the environmental data.

7. A system for facilitating monitoring of an individual based on at least one wearable device, the system comprising:
a communication device configured for:
receiving at least one physiological data from a user device associated with the individual, wherein the user device is configured for receiving the at least one physiological data from at least one wearable device worn by the individual, wherein the at least one wearable device comprises at least one physiological sensor configured for generating the at least one physiological data, wherein the at least one physiological data is associated with a user identifier of the individual; and
transmitting at least one notification to at least one watcher device associated with at least one watcher identifier;
a processing device configured for:
analyzing the at least one physiological data based on at least one analyzing criterion; and
generating at least one notification based on the analyzing; and
a storage device configured for:
retrieving the at least one analyzing criterion based on the user identifier;
retrieving the at least one watcher identifier based on the user identifier, wherein the at least one watcher identifier is associated with at least one watcher registered to receive the at least one notification in association with the individual;
the communication device is further configured for receiving at least one response from at least one of the user device and the at least one watcher device, wherein the at least one response corresponds to the at least one notification;
the processing device is further configured for:
performing machine learning on each of the at least one physiological data, the at least one notification and the at least one response in association with the user identifier; and
generating the at least one analyzing criterion based on the machine learning, wherein the storage device is further configured for storing the at least one analyzing criterion;
the storage device is further configured for storing a first physiological data corresponding to a first time period;
the processing device is further configured for:
analyzing the first physiological data;
generating a user model based on the analyzing of the first physiological data; and
predicting a second physiological data corresponding to a second time period based on the user model, wherein the at least one analyzing criterion is based on the second physiological data;
the communication device is further configured for receiving location data corresponding to the individual, wherein the at least one notification further comprises the location data, and wherein the at least one wearable device and the user device comprises a location sensor; and
the communication device is further configured for transmitting the at least one notification to the at least one wearable device, wherein the at least one wearable device is communicatively coupled to a pill dispenser configured for dispensing at least one pill based on the at least one notification.

8. The system of claim 7, wherein the user device comprises the at least one wearable device.

9. The system of claim 7, wherein the communication device is further configured for receiving medical data of the individual from at least one clinical database associated with the individual, wherein the processing device is further configured for:
analyzing the medical data; and
generating the at least one analyzing criterion based on the analyzing of the medical data.

10. The system of claim 7, wherein the communication device is further configured for:
receiving a first analyzing criterion from a first watcher device;
receiving a second analyzing criterion from a second watcher device, wherein the at least one analyzing criterion comprises the first analyzing criterion and the second analyzing criterion, wherein the at least one notification comprises a first notification and a second notification;
transmitting the first notification to the first watcher device; and
transmitting the second notification to the second watcher device.

11. The system of claim 7, wherein the at least one watcher device comprises a first watcher device and a second watcher device, wherein the communication device is further configured for:
receiving a first response indication of a first response from the first watcher device, wherein the first response corresponds to the at least one notification; and
transmitting the first response indication to the second watcher device.

12. The system of claim 7, wherein the communication device is further configured for receiving at least one of motion data and environmental data from at least one of the user device and the at least one wearable device comprising at least one of a motion data sensor and an environmental sensor, wherein the generating of the at least one notification is further based on at least one of the motion data and the environmental data, wherein the at least one notification further comprises at least one of the motion data and the environmental data.

* * * * *